(12) United States Patent
Groothuis et al.

(10) Patent No.: US 12,102,532 B2
(45) Date of Patent: Oct. 1, 2024

(54) SYSTEMS AND METHODS FOR TREATING LUMINAL VALVES

(71) Applicant: ReNiva, Inc., Mountain View, CA (US)

(72) Inventors: Adam Groothuis, Swampscott, MA (US); Adrian Ebner, Asuncion (PY); Peter Markham, Kingston, NH (US); Elazer Edelman, Brookline, MA (US)

(73) Assignee: ReNiva, Inc., Mountain View, CA (US)

( * ) Notice: Subject to any disclaimer, the term of this patent is extended or adjusted under 35 U.S.C. 154(b) by 617 days.

(21) Appl. No.: 16/943,606

(22) Filed: Jul. 30, 2020

(65) Prior Publication Data
US 2021/0015615 A1 Jan. 21, 2021

Related U.S. Application Data

(63) Continuation of application No. 16/036,618, filed on Jul. 16, 2018, now abandoned.

(51) Int. Cl.
*A61F 2/24* (2006.01)

(52) U.S. Cl.
CPC .......... *A61F 2/2445* (2013.01); *A61F 2/2412* (2013.01); *A61F 2/2418* (2013.01); *A61F 2/2466* (2013.01); *A61F 2210/0014* (2013.01); *A61F 2220/0008* (2013.01); *A61F 2220/0016* (2013.01); *A61F 2230/0013* (2013.01); *A61F 2250/0039* (2013.01)

(58) Field of Classification Search
CPC ............................. A61F 2/2463; A61F 2/2469
See application file for complete search history.

(56) References Cited

U.S. PATENT DOCUMENTS

| | | | |
|---|---|---|---|
| 4,275,469 A | 6/1981 | Gabbay |
| 4,994,077 A | 2/1991 | Dobben |
| 5,538,510 A | 7/1996 | Fontirroche et al. |
| 5,906,619 A | 5/1999 | Olson et al. |
| 5,925,063 A | 7/1999 | Khosravi |
| 6,338,740 B1 | 1/2002 | Carpentier |
| 6,419,696 B1 | 7/2002 | Ortiz et al. |
| 6,436,135 B1 | 8/2002 | Goldfarb |
| 6,464,683 B1 | 10/2002 | Samuelson et al. |
| 6,488,694 B1 | 12/2002 | Lau et al. |
| 6,705,585 B1 | 3/2004 | Roy |
| 6,869,444 B2 | 3/2005 | Gabbay |
| 6,974,476 B2 | 12/2005 | McGuckin et al. |
| 8,292,938 B2 | 10/2012 | Case |
| 8,348,997 B2 | 1/2013 | Thompson et al. |

(Continued)

OTHER PUBLICATIONS

Non-Final Office Action issued in related U.S. Appl. No. 13/868,226, filed Dec. 17, 2013.

(Continued)

*Primary Examiner* — Megan Y Wolf
(74) *Attorney, Agent, or Firm* — Levine Bagade Han LLP

(57) ABSTRACT

A partial valve prosthesis includes a framework configured for following a shape of a portion of the native valve annulus when implanted into the native valve annulus, the framework including securement features for anchoring the framework to an inner periphery of the native valve annulus and retaining at least one leaflet configured to replace a corresponding one of the plurality of native leaflets; and at least one leaflet secured to the framework. Additional embodiments and methods are disclosed.

25 Claims, 14 Drawing Sheets

(56) References Cited

U.S. PATENT DOCUMENTS

| | | |
|---|---|---|
| 8,388,599 B2 | 3/2013 | Warnack |
| 8,894,704 B2 | 11/2014 | Groothuis et al. |
| 10,022,222 B2 | 7/2018 | Groothuis et al. |
| 2004/0193261 A1* | 9/2004 | Berreklouw .......... A61F 2/2409 623/2.11 |
| 2004/0225353 A1 | 11/2004 | McGuckin, Jr. et al. |
| 2005/0038509 A1 | 2/2005 | Ashe |
| 2005/0107871 A1* | 5/2005 | Realyvasquez ....... A61F 2/2454 623/2.11 |
| 2005/0137701 A1 | 6/2005 | Salahieh et al. |
| 2005/0228495 A1 | 10/2005 | Macoviak |
| 2006/0020332 A1 | 1/2006 | Lashinski et al. |
| 2006/0020334 A1 | 1/2006 | Lashinski et al. |
| 2006/0259135 A1 | 11/2006 | Navia et al. |
| 2006/0271081 A1 | 11/2006 | Realyvasquez |
| 2008/0177382 A1 | 7/2008 | Hyde et al. |
| 2008/0183273 A1 | 7/2008 | Mesana et al. |
| 2008/0275550 A1 | 11/2008 | Kheradvar et al. |
| 2009/0005863 A1 | 1/2009 | Goetz et al. |
| 2010/0168844 A1 | 7/2010 | Toomes et al. |
| 2010/0217385 A1 | 8/2010 | Thompson et al. |
| 2011/0004296 A1 | 1/2011 | Lutter et al. |
| 2011/0112630 A1 | 5/2011 | Groothuis et al. |
| 2013/0310924 A1 | 11/2013 | Groothuis et al. |
| 2014/0088696 A1 | 3/2014 | Figulla et al. |
| 2014/0222142 A1 | 8/2014 | Kovalsky et al. |
| 2014/0309727 A1* | 10/2014 | Lamelas ............... A61F 2/2412 623/2.11 |
| 2015/0119981 A1* | 4/2015 | Khairkhahan ........ A61F 2/2466 623/2.36 |
| 2015/0272737 A1 | 10/2015 | Dale et al. |
| 2016/0310267 A1 | 10/2016 | Zeng et al. |
| 2016/0361161 A1 | 12/2016 | Braido et al. |
| 2017/0258589 A1 | 9/2017 | Pham et al. |
| 2017/0333187 A1 | 11/2017 | Hariton et al. |

OTHER PUBLICATIONS

Non-Final Office Action issued in corresponding U.S. Appl. No. 12/899,231, filed May 10, 2013.
Final Office Action issued in corresponding U.S. Appl. No. 12/899,231, filed Jan. 31, 2014.
Non-Final Office Action issued in corresponding U.S. Appl. No. 12/899,231, filed Jun. 5, 2015.
Final Office Action issued in corresponding U.S. Appl. No. 12/899,231, Jan. 12, 2016.
Final Office Action issued in corresponding U.S. Appl. No. 12/899,231, Nov. 17, 2017.
Final Office Action issued in related U.S. Appl. No. 13/868,226, Aug. 27, 2014.

* cited by examiner

SYSTEMS AND METHODS FOR TREATING LUMINAL VALVES

CROSS REFERENCE TO RELATED APPLICATIONS

The present patent application is a continuation-in-part of and claims the benefit of priority to U.S. patent application Ser. No. 16/036,618 filed on Jul. 16, 2018. This application is related to U.S. patent application Ser. No.: 12/899,231, filed Oct. 6, 2010 and U.S. Provisional Patent Application No. 61/249,020, filed on Oct. 6, 2009. Each of the aforementioned patent applications is incorporated by reference herein for any purpose whatsoever.

BACKGROUND OF THE INVENTION

1. Field of the Invention

The subject matter disclosed herein relates to systems and methods for treating luminal valves, and in particular, to methods and systems for partial or complete replacement of luminal valves.

2. Description of the Related Art

Recently, there has been increasing consideration given to the possibility of using, as an alternative to traditional cardiac-valve prostheses, valves designed to be implanted using minimally-invasive surgical techniques or endovascular delivery (so-called "percutaneous valves"). Implantation of a percutaneous valve is a far less invasive act than the surgical operation required for implanting traditional cardiac-valve prostheses.

In order to provide some context, aspects of cardiac anatomy and existing technology are introduced.

FIG. 1 is a cross-sectional view depicting aspects of cardiac anatomy. Included in the depiction are the aortic valve, the mitral valve and the tricuspid valve, along with the left fibrous trigone and the right fibrous trigone.

The mitral valve, also known as the bicuspid valve or left atrioventricular valve, is a valve with two flaps. The mitral valve lies between the left atrium and the left ventricle. The mitral valve along with the tricuspid valve are known collectively as the atrioventricular valves because they lie between the atria and the ventricles of the heart.

In normal conditions, blood flows through an open mitral valve during diastole with contraction of the left atrium, and the mitral valve closes during systole with contraction of the left ventricle. The mitral valve opens and closes because of pressure differences, opening when there is greater pressure in the left atrium than ventricle, and closing when there is greater pressure in the ventricle than atrium.

In abnormal conditions, blood may flow backwards through the valve (mitral regurgitation) or the mitral valve may be narrowed (mitral stenosis). Rheumatic heart disease often affects the mitral valve. The valve may also prolapse with age, and be affected by infective endocarditis.

The mitral valve is typically 4 to 6 square centimeters (0.62 to 0.93 sq in) in area, and sits in the left heart between the left atrium and the left ventricle. The mitral valve has two leaflets, an anterior leaflet and a scalloped posterior leaflet. The opening of the mitral valve is surrounded by a fibrous ring known as the mitral annulus. The posterior leaflet of the mitral valve covers approximately two-thirds of the valve (imagine a crescent moon within the circle, where the crescent represents the posterior cusp). The valve leaflets are prevented from prolapsing into the left atrium by the action of chordae tendineae. The chordae tendineae are inelastic tendons attached at one end to papillary muscles in the left ventricle, and at the other to the valve leaflet. Papillary muscles are finger-like projections from the wall of the left ventricle. The chordae tendineae prevent the eversion, prolapse by becoming tense, thus pulling the flaps and holding them in closed position.

When the left ventricle contracts, the pressure in the ventricle forces the valve to close, while the tendons keep the leaflets coapting together and prevent the valve from opening in the wrong direction (thus preventing blood to flow back to the left atrium). Each chord has a different thickness. The thinnest ones are attached to the free leaflet margin, whereas thickest ones (strut chords) are attached quite away from the free margin. This disposition has important effects on systolic stress distribution physiology.

The mitral annulus is a fibrous ring that is attached to the mitral valve leaflets. Unlike conventional prosthetic valves, the mitral annulus is not continuous. The mitral annulus is saddle shaped and changes in shape throughout the cardiac cycle. The annulus contracts and reduces its surface area during systole to help provide complete closure of the leaflets. Expansion of the annulus can result in leaflets that do not join soundly together, leading to functional mitral regurgitation. Similarly, the tricuspid annulus exhibits an odd or irregular shape. As a result, conventional prosthetic valves do a poor job of mimicking the physiology of the mitral valve and the tricuspid valve and therefore perform poorly.

The normal diameter of the mitral annulus is 2.7 to 3.5 centimeters (1.1 to 1.4 in), and the circumference is 8 to 9 centimeters (3.1 to 3.5 in). Microscopically, there is no evidence of an annular structure anteriorly, where the mitral valve leaflet is contiguous with the posterior aortic root.

FIG. 2 is a cross-sectional schematic view of the mitral annulus with a portion of a conventional or prior art prosthetic valve disposed therein. The mitral annulus is a fibrous ring to which the natural mitral valve leaflets are attached. As noted above, prior art prostheses used for the mitral valve are continuous and therefore do not mimic the physiology well. In this illustration, an imaginary axial centerline, R, is shown for purposes of convention.

Various other embodiments of prior art prosthetic valves are depicted in FIG. 3. Each of the prior art prosthetic valves 10 depicted include features for securing the respective prosthetic valve into the designated annulus. In FIG. 3A, the prior art prosthetic valve 10 includes a stent like structure 12 with a radially expandable framework. The stent like structure 12 that opens to a series of petals 13, each petal 13 supporting an optional layer of protective material 14. Once surgically implanted, the radially expandable framework will extend radially beyond the annulus on the atrial side and also the ventricular side along the annulus. In between the atrial side radial extension and the ventricular side radial extension is a waist 15. Generally, the waist 15 is sized to fit snuggly along the annulus of the ventricle and atrium.

Each of the atrial side radial extension and the ventricular side radial extension project radially outwardly from the imaginary axial centerline, R, such that the prior art prosthetic valve 10 is secured into the annulus and (hopefully) exhibits minimal leakage between the framework and the annulus.

In FIG. 3B, the prior art prosthetic valve 10 includes a body 23 that includes a series of petals 13, each petal 13 extending radially outward from an imaginary axial centerline, R. Each of the petals 13 effectively enhances a radius of the body 23 thus securing the body 23 within the mitral annulus by expanding along the ventricular surface. Also included on an atrial side of the prior art prosthetic valve 10 are a series of corkscrew style anchors 25. Each of the corkscrew style anchors 25 will embed within the atrial side of the annulus, thus securing the prior art prosthetic valve 10.

In FIG. 3C, another embodiment of a prior art prosthetic valve 10 is shown. In this example, the prior art prosthetic valve 10 includes a dual stent with an outer stent 41 and an inner stent 42. The outer stent 41 and the inner stent 42 may be interlocked, and each one expandable on a respective side of the given annulus. Together, the outer stent 41 and the inner stent 42 cooperate to secure the prior art prosthetic valve 10 into the annulus into which the prior art prosthetic valve 10 is to be installed.

In FIG. 3D, yet another of a prior art prosthetic valve 10 is shown. Included is a side-view (top diagram) and a perspective view from the bottom (bottom diagram). In this embodiment, the prior art prosthetic valve 10 includes a stent 12 with a radially expandable framework that forms a cup region. Generally, the cup region is realized when the radially expandable framework is surgically implanted and a series of petals 13 extend radially outwardly, up into the atrium and along the atrial surface.

These expandable prior art prosthetic valves 10 typically include an anchoring structure or armature, which is able to support and fix the valve prosthesis by either fixing the native leaflet or fibrous regions of the annulus (i.e. Trigones, or commissures) in the implantation position, and prosthetic valve elements, generally in the form of leaflets or flaps, which are connected to the anchoring structure and are able to regulate blood flow.

However, these and other such systems have typically called for surgical delivery of large implantable devices. Further, such devices poorly mimic the physiology of the natural valve. The impact of major surgery and the poor physiological correlation often leads to compromised health and other complications.

The foregoing examples of prior art prosthetic valves 10 are better suited to complete replacement of aortic valve as the annulus there is substantially circular. Both the mitral annulus (as discussed above) and the annulus for the tricuspid valve are saddle shaped and change in shape throughout the cardiac cycle. The prior art prosthetic valves 10 are poor options for use in these valve repairs.

What are needed are methods and apparatus for percutaneous delivery of improved replacement valves that result in minimal adverse effects on the patient.

SUMMARY OF THE INVENTION

In one embodiment, a partial valve prosthesis for replacing a portion of a native luminal valve is disclosed. The native luminal valve defining a native valve annulus and a plurality of native leaflets, the partial valve prosthesis includes a framework configured for following a shape of a portion of the native valve annulus when implanted into the native valve annulus, the framework including securement features for anchoring the framework to an inner periphery of the native valve annulus and retaining at least one leaflet configured to replace a corresponding one of the plurality of native leaflets; and at least one leaflet secured to the framework.

The native luminal valve may include one of a mitral valve, a tricuspid valve and an aortic valve. The framework may include at least one of: a shape memory material, a nickel titanium alloy, and a biocompatible material. The securement features may include at least one of tines, clamps, petals, corkscrew anchors, cooperative stents, a cupped side and combination thereof. The securement features may be configured to cooperate with at least one intermediate structure. The intermediate structure may include one of a post, a fixation device, a clamp and a suture. The clamp may include at least one of a perforation and a loop at a terminal end. A protective sheathing may be disposed thereover. The protective sheathing may include at least one of polytetrafluoroethylene (PTFE), polyethylene terephthalate (PET or PETE), polyester or another biocompatible material.

In another embodiment, a partial valve prosthesis for replacing a portion of a native luminal valve, the native luminal valve defining a native valve annulus and a plurality of native leaflets is provided. The partial valve prosthesis including a framework configured for following a shape of a portion of the native valve annulus when implanted into the native valve annulus, the framework including an array of clamps attached thereto, each of the clamps configured for clamping about the native valve leaflets and or annulus and anchoring the framework to an inner periphery of the native valve leaflets or annulus, the framework further configured for retaining at least one leaflet configured to replace a corresponding one of the plurality of native leaflets; and at least one leaflet secured to the framework.

At least one of the clamps may include at least one of a perforation and a loop at a terminal end. At least one of the clamps may be configured for securement with at least one of a post and suture material. The native luminal valve may include one of a mitral valve, a tricuspid valve and an aortic valve.

In yet another embodiment, a method for implanting a partial valve prosthesis for replacing a portion of a native luminal valve, the native luminal valve defining a native valve annulus and a plurality of native leaflets is provided. The method includes using a device configured for percutaneous delivery, disposing along the native valve annulus a framework that is configured for following a shape of a portion of the native valve annulus, the framework including securement features for anchoring the framework to an inner periphery of the native valve leaflet and or annulus and retaining at least one leaflet configured to replace a corresponding one of the plurality of native leaflets; securing the framework into the native valve annulus.

Securing may include at least one of suturing, clamping and posting the framework into place.

It is to be understood that the foregoing general description and the following detailed description are exemplary and are intended to provide further explanation of the invention claimed.

The accompanying drawings, which are incorporated in and constitute part of this specification, are included to illustrate and provide a further understanding of the method and system of the invention. Together with the description, the drawings serve to explain principles of the invention.

BRIEF DESCRIPTION OF THE DRAWINGS

The features and advantages of the invention are apparent from the following description taken in conjunction with the accompanying drawings in which.

DETAILED DESCRIPTION OF THE INVENTION

Figure 1:
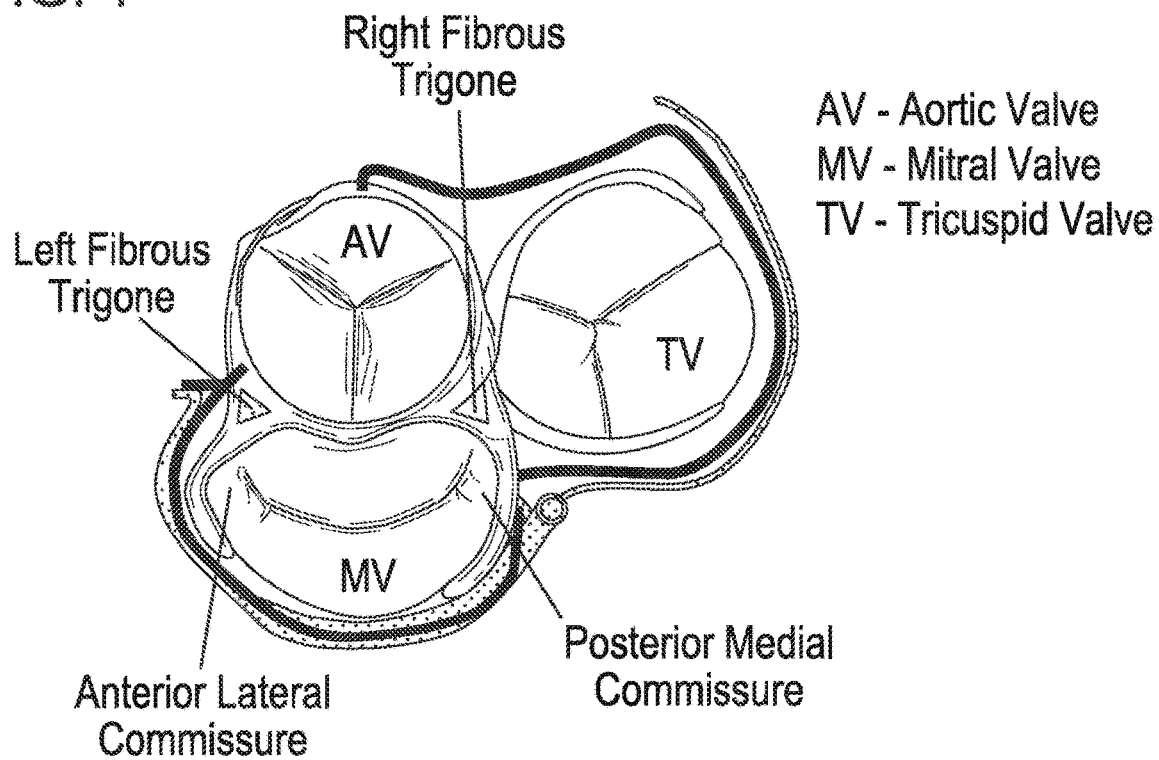
FIG. 1 is a cross-sectional view depicting aspects of cardiac anatomy.
Figure 2:
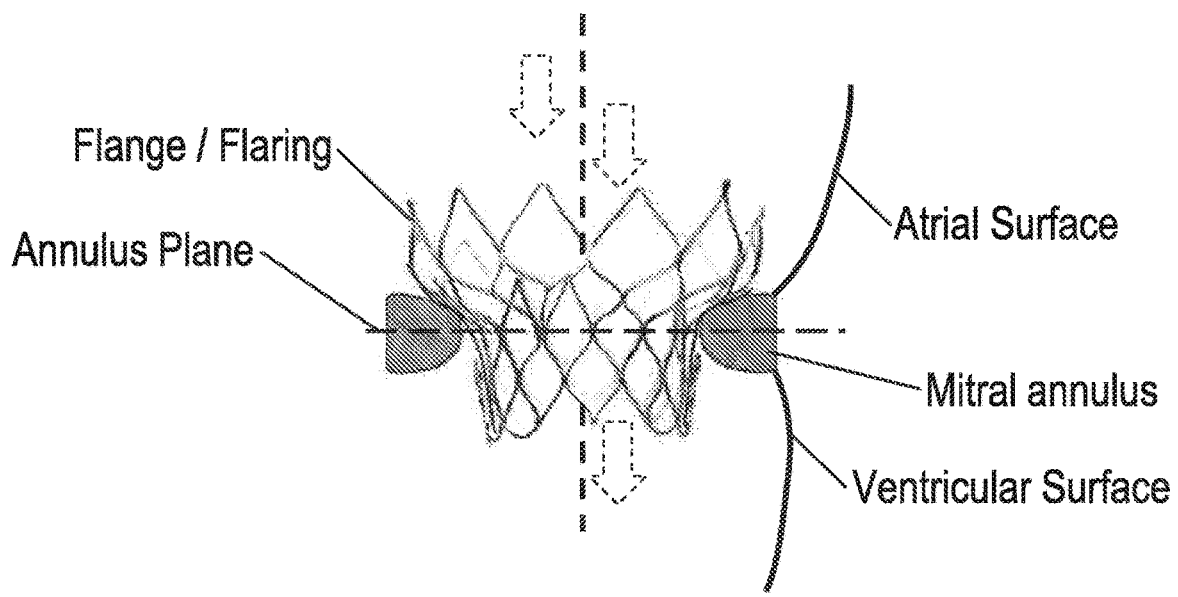
FIG. 2 is a cross-sectional schematic view of a prior art artificial mitral valve disposed in-situ.
Figure 3A:
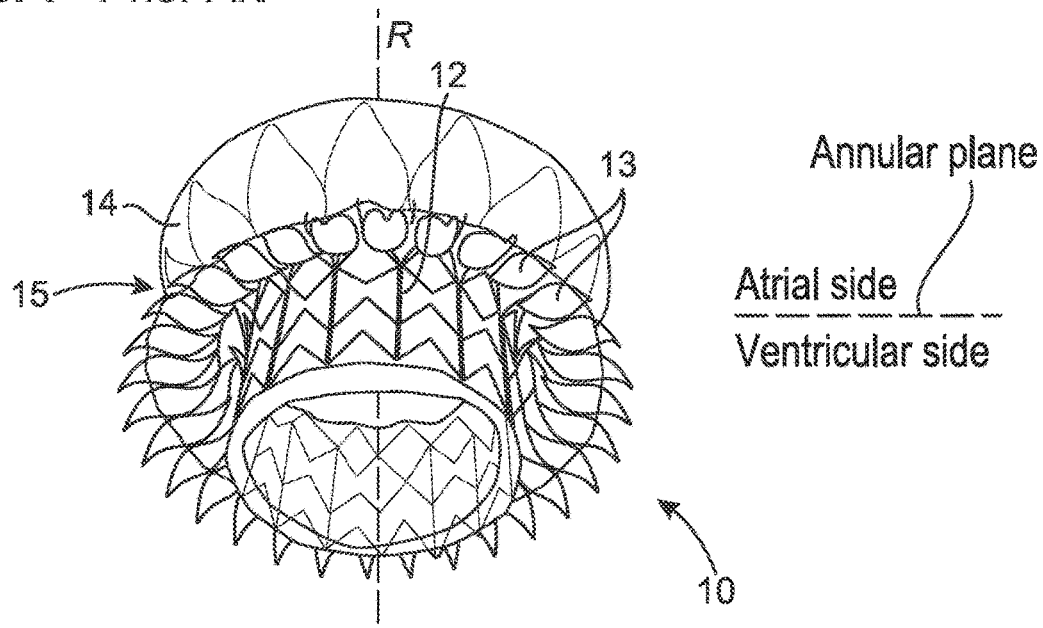
FIGS. 3A, 3B, 3C and 3D, collectively referred to herein as FIG. 3, depict prior art valve devices.
Figure 3B:
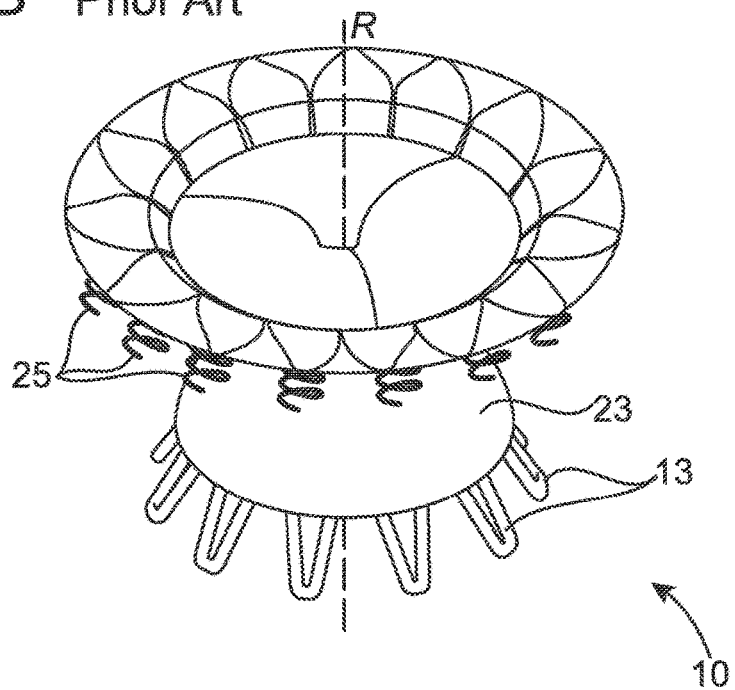
Figure 3C:
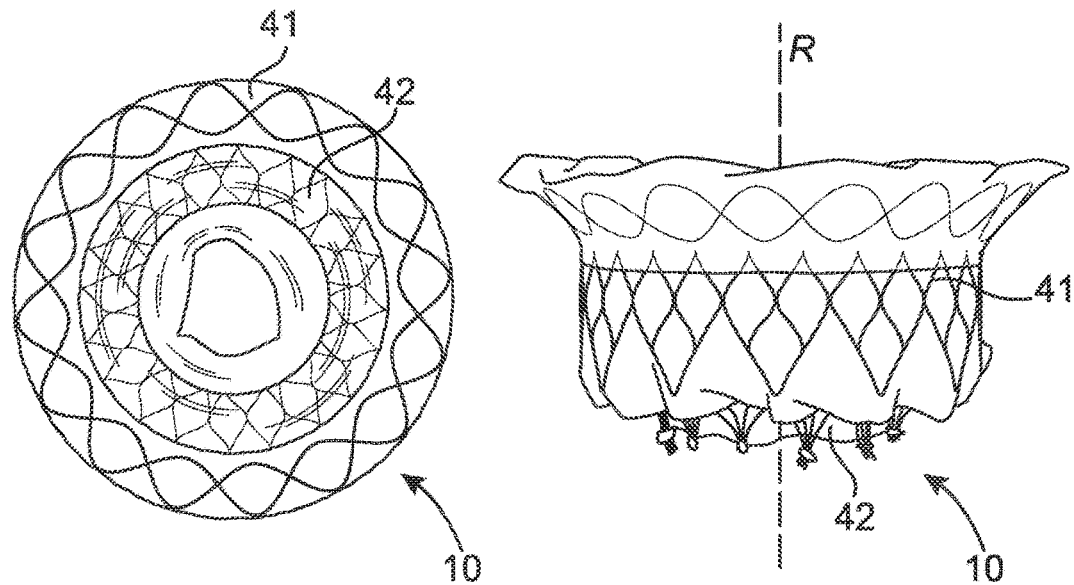
Figure 3D:
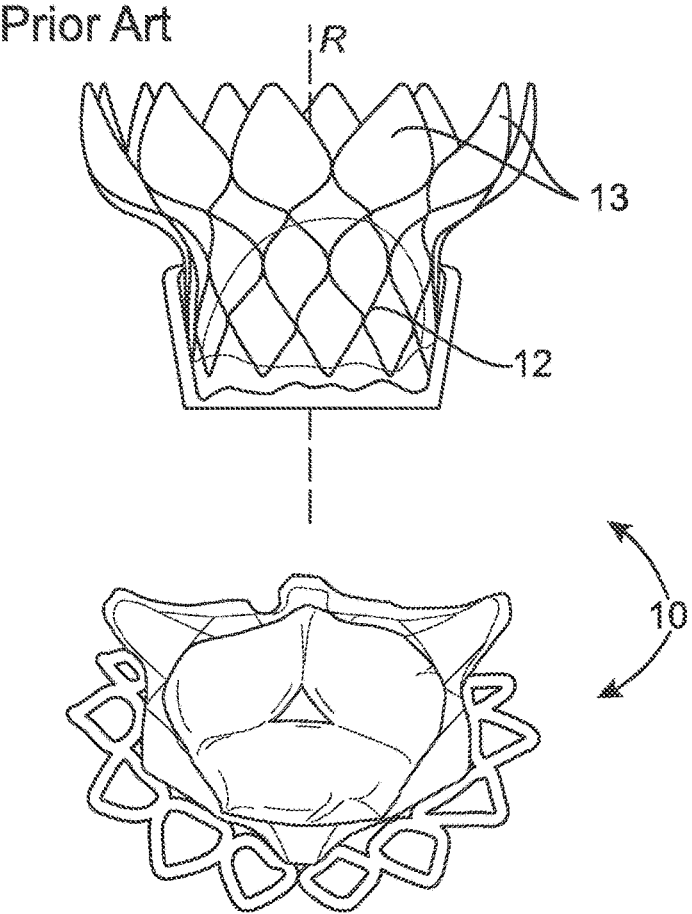

Disclosed herein are embodiments of partial valve prostheses. The partial valve prostheses are suited for percutaneous deployment. Generally, deployment calls for deforming a given partial valve prosthesis such that implantation is minimally invasive to the recipient. Advantageously, each embodiment of the partial valve prostheses are much less invasive than prior art prostheses. The design of the partial valve prostheses, taken in combination with less invasive techniques for implantation, results in substantially better patient outcomes than were previously achieved in the prior art.

Generally, each partial valve prosthesis is suited for percutaneous delivery. The percutaneous delivery may make use of specialized tooling, such as the catheter disclosed in the related patent references incorporated herein by reference in their entirety. The catheter disclosed therein, and partially reviewed herein, is but one example of a delivery device for delivering the partial valve prosthesis to a surgical site at a valve annulus.

As discussed elsewhere herein, and in the related patent references incorporated herein by reference in their entirety, the partial valve prostheses disclosed herein are not limited to use with cardiac valves such as mitral valves or tricuspid valves. In short, the partial valve prostheses may be used wherever deemed appropriate, and may be used alone or in combination.

Generally, the partial valve prostheses disclosed herein make use of various materials. For example, the partial valve prostheses may incorporate a sheathing material such as polytetrafluoroethylene (PTFE), polyethylene terephthalate (PET or PETE), polyester or other similar biocompatible materials. Generally, the sheathing may be disposed about a framework for the partial valve prostheses in order to better seal the device when in use, to limit any biological interaction between the framework and the recipient, to limit bacterial growth, to assist with physical structure and/or anchoring or for any other purpose deemed appropriate. Additionally, various framework materials may be used.

The framework may be fabricated from any material deemed appropriate. In some embodiments, the framework includes nickel titanium, also known as Nitinol (part of shape memory alloy), is a metal alloy of nickel and titanium, where the two elements are present in roughly equal atomic percentages e.g. Nitinol 55, Nitinol 60. Nitinol alloys exhibit two closely related and unique properties: shape memory effect (SME) and super-elasticity (SE; also called pseudo-elasticity, PE). Shape memory is the ability of NITINOL to undergo deformation at one temperature, then recover its original, un-deformed shape upon heating above a "transformation temperature." Other materials may be used as deemed appropriate. For example, various polymeric materials may be used. As a more specific example, in some embodiments, NYLON™ or similar materials may be used. NYLON™ is a generic designation for a family of synthetic polymers, based on aliphatic or semi-aromatic polyamides. NYLON™ is a thermoplastic silky material that can be melt-processed into fibers, films or shapes. Generally, the framework includes biocompatible material. Tissue, such as from a suitable porcine or bovine donor or a cadaver, may be used.

As an illustrative non-limiting example, devices and associated methods described herein may be used to treat, among other things, vascular valve dysfunction and/or insufficiency in patients with Congestive Heart Failure (CHF) and or venous leg edema with symptoms that may include, for example, mitral regurgitation and venous insufficiency. In such cases, valve dysfunction occurs because of dilation, or enlargement, of the heart and/or veins and causes dysfunction of the valves. Venous insufficiency leads to edema of the legs while mitral regurgitation leads to decreased ventricular function. These conditions necessitate a need for less invasive procedures. Percutaneous procedures enable a non-surgical approach to treat symptoms via a partial or complete valve replacement in a stepwise fashion. Current percutaneous procedures and or devices are limited in their ability to treat the full potential patient populations. Notably, it is observed herein that a partial and/or complete replacement may provide potential benefit over surgical and percutaneous methods for repair or complete replacement.

Current procedure requires one to two access points from the femoral or jugular vein. In accordance with the teachings herein, it is possible to use percutaneous approaches to partially or completely replace heart valves or venous valves with a valve prosthesis by way of a transceptal approach or from a femoral retrograde approach. Using such approaches it becomes possible, for example, to achieve a partial or complete replacement of the mitral valve in a stepwise fashion using percutaneous methods. In some embodiments, the components disclosed herein are delivered via at least one of the subclavian vein and the jugular vein.

The approaches herein may be used, for example, for treatment of patients with class 1 and Class 2 CHF. These classes of patients currently are not good surgical candidates. Opportunities thus exist to treat these patients percutaneously and in conjunction with other percutaneous procedures. Patients with venous edema represent a significantly larger patient population than CHF. Current methods to treat edema include pressure bandages in order to elevate symptoms. It is believed that the disclosed embodiments provide a novel approach that can correct valve dysfunction.

Thus, in accordance with one aspect of the disclosed embodiments, a catheter is provided including an elongate body, a retractable sheath, and including a deployable valve prosthesis. For purpose of explanation and illustration, and not limitation, a partial view of an exemplary embodiment of a catheter used with an exemplary embodiment of the partial valve prosthesis is shown in FIGS. 4 through 13 and is designated generally by reference character 100. It should be noted that the embodiments presented and described with regard to FIG. 4 through FIG. 13 are generally referred to as a "first" embodiment. This reference is for convenience and introduction only. Embodiments appearing subsequent to FIG. 4 through FIG. 13 are generally referred to as additional or other embodiments. It should be understood that many variations (embodiments) may be realized. Any statements against interest are not to be construed and may only be implied or limited to purposes of facilitating an introduction to the technology disclosed herein.

Figure 4:
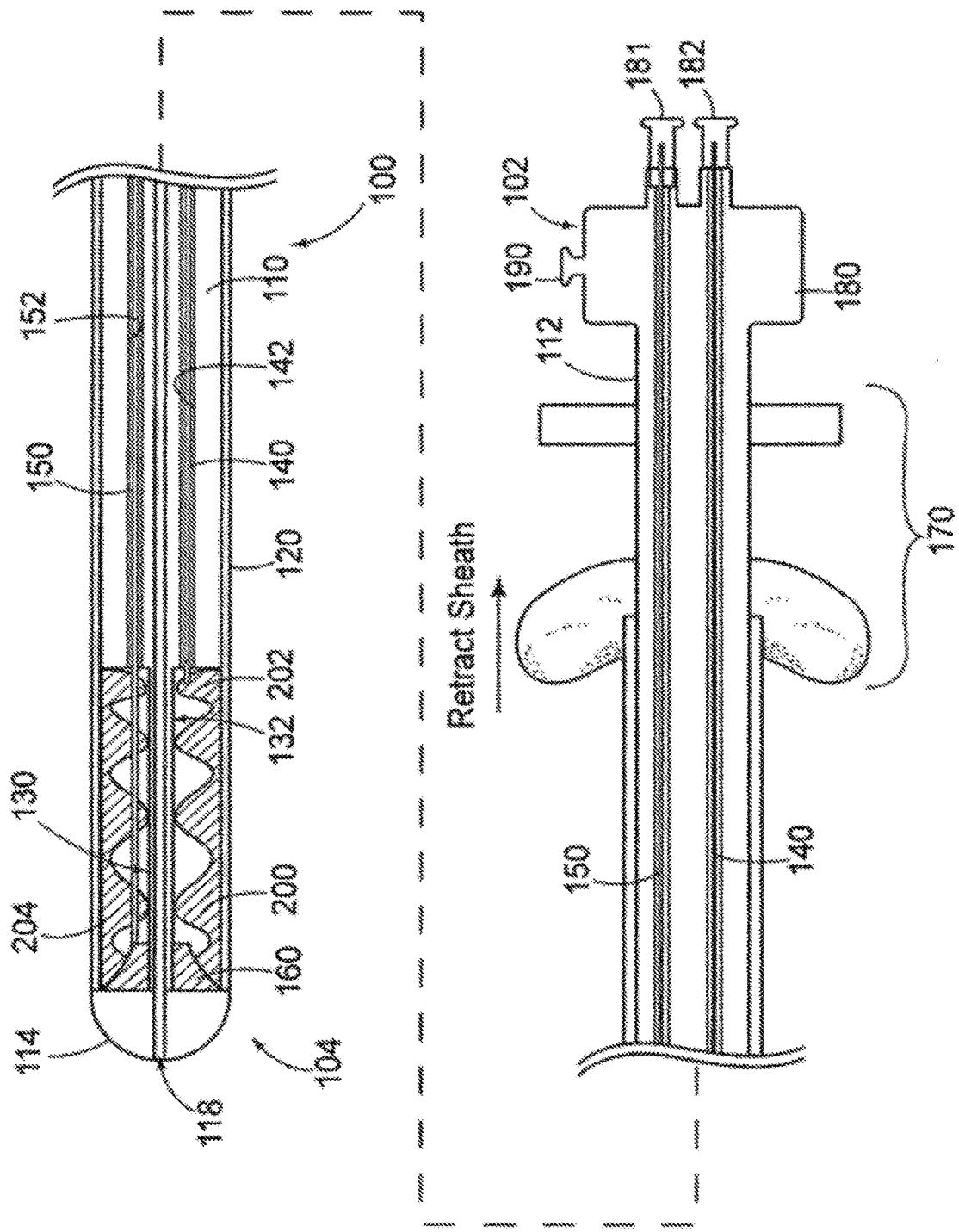
FIG. 4, along with FIG. 5 through FIG. 13, depict aspects of an exemplary method for delivering an first embodiment of a deployable valve prosthesis using a catheter.

As depicted in FIG. 4, catheter 100 includes an elongate body 110 having a proximal end 112, a distal end 114, and a retractable sheath 120 mounted on the elongate body 110 proximate the distal end 114. The sheath 120 and elongate body 120 cooperate to define a first annularly-shaped compartment 130 between the body and sheath for receiving a valve prosthesis 200, described in detail below.

As further depicted in FIG. 4, the catheter 100 includes apparatus to facilitate deploying the valve prosthesis 200. For purposes of illustration and not limitation, as illustrated herein, such apparatus includes a first linkage 140. First linkage 140 extends from a proximal region 132 of the compartment 130 toward the proximal end 102 of the catheter 100 to help deploy valve prosthesis 200. As depicted in FIG. 4, catheter 100 further includes a second linkage 150 extending from a distal region 134 of the compartment 130 toward the proximal end 102 of the catheter 100 to help deploy the valve prosthesis 200.

As depicted in FIG. 4, catheter 100 further includes a first example of a valve prosthesis 200. The exemplary valve prosthesis 200 is mounted in the compartment 130, the prosthesis 200 having a proximal end 202 attached to the first linkage 140 and a distal end 204 attached to the second linkage 150. Prosthesis 200, as illustrated, is presented as a valve prosthesis 200. Other embodiments of prostheses are described below.

In an un-deployed state, prosthesis 200 is in a generally longitudinal configuration. However, during and after deployment, as illustrated in FIGS. 7(B)-13, prosthesis 200 may have a generally annular configuration. In the embodiment depicted in FIG. 10, upon deployment, prosthesis 200 includes a peripheral region 206 including reinforcing structural material 212 such as scaffolding, and a leaflet 208 having an edge 209 made, for example, from a polymeric membrane 216. The structural material may include metallic and/or polymeric materials. Preferably, structural material 212 includes shape memory material, such as various alloys of nickel and titanium. It will be recognized that a variety of structures can be used for structural material 212 without departing from the spirit or scope of the disclosed embodiments. Concerning membrane 216, a variety of biocompatible materials can be used, such as ePTFE described, for example, in U.S. Pat. No. 6,436,135, which is incorporated by reference herein it its entirety. A variety of other polymeric, composite or biological materials may be used. For example, if desired, cellular content may be used and/or structural components from cadavers may be used as long as the materials are suitable for implantation.

As further depicted in FIG. 4, catheter 100 may further include a guide 160 for directing the path of travel of the first linkage 140 and second linkage 150 to facilitate deployment of the valve prosthesis 200. As depicted, guide 160 is generally bell-shaped, and acts to cause linkages 140, 150 to splay apart during deployment of prosthesis 200 to help prosthesis 200 to take on an arcuate shape. Particularly, a pull wire 162 or similar structure can be provided to advance guide 160 proximally to facilitate deployment. However, it will be recognized that guide 160 need not be provided. For example, if shape memory material is used to make prosthesis 200 and/or linkages 140, 150, deployment may be facilitated by such components changing shape by retracting sheath 120 proximally and by manipulating linkages 140, 150 along a proximal/distal direction, as well as rotationally.

Figure 6:
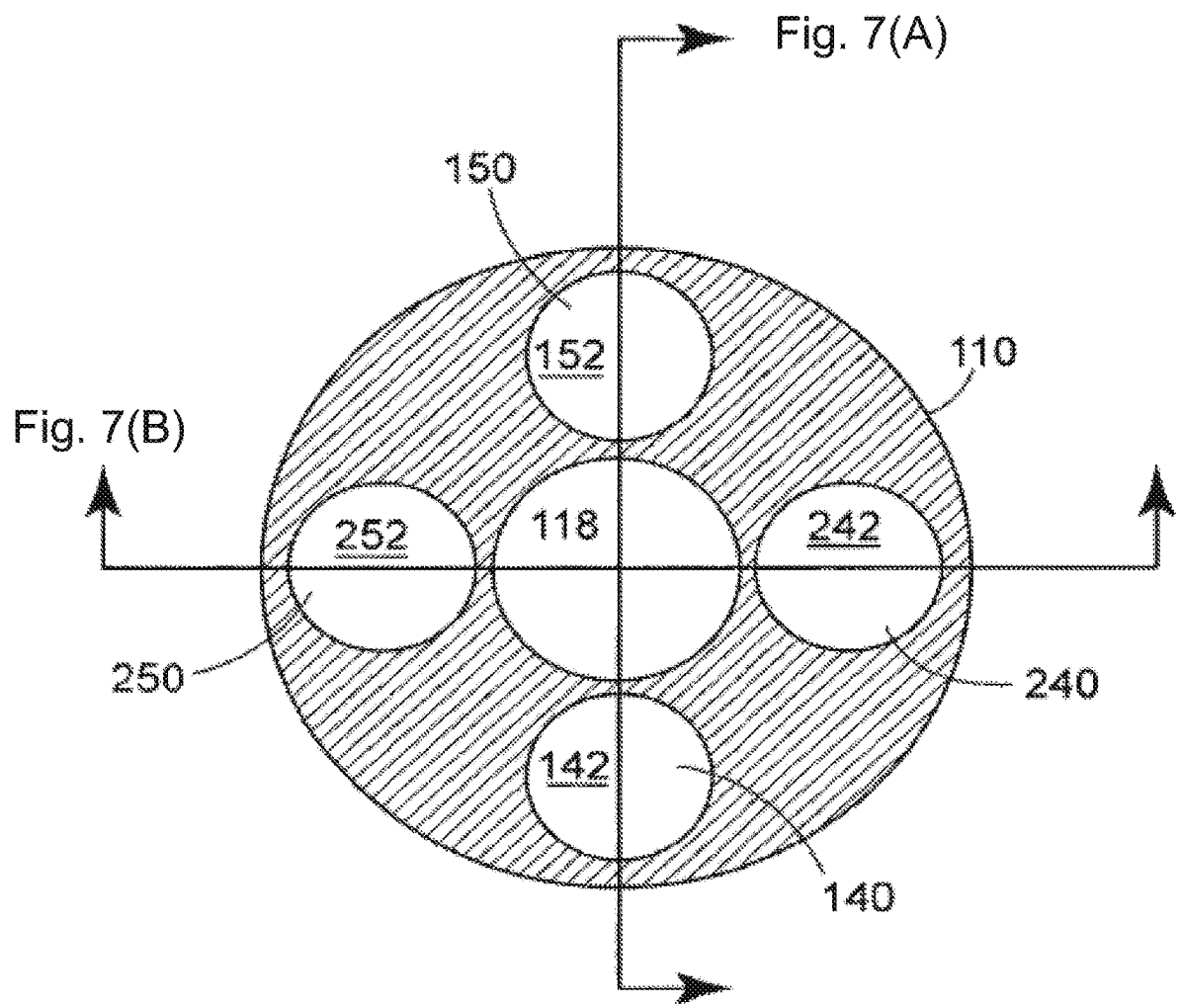

Linkages 140, 150 (and 240, 250, described below) may be made from a variety of materials, such as hypotubes made from stainless steel (and having a very small profile), or may be solid metallic or composite members, such as carbon fiber reinforced materials. As depicted in FIG. 6, inner member 110 may include a variety of lumins along its length, such as for advancing or retracting linkages 140, 150 (and 240, 250), as well as for pull wire 162, or for a guidewire. Specifically, a guidewire lumin 118 is provided, if desired. It will also be recognized that catheter 100 can be delivered in a guiding catheter, and need not be provided with its own guidewire lumin 118.

Referring again to FIG. 4, sheath 120 is preferably adapted and configured to be retracted along a longitudinal axis of the catheter to expose the valve prosthesis using an actuator 170, described in more detail below. The first linkage 140 and second linkage 150 are preferably adapted and configured to deploy the valve prosthesis 200 when the sheath 120 is in a retracted position by advancing the second linkage 150 in a proximal direction and by advancing the first linkage 140 in a distal direction. An example of a method of deployment of valve prosthesis 200 using catheter 100 is described in detail below.

Figure 5:
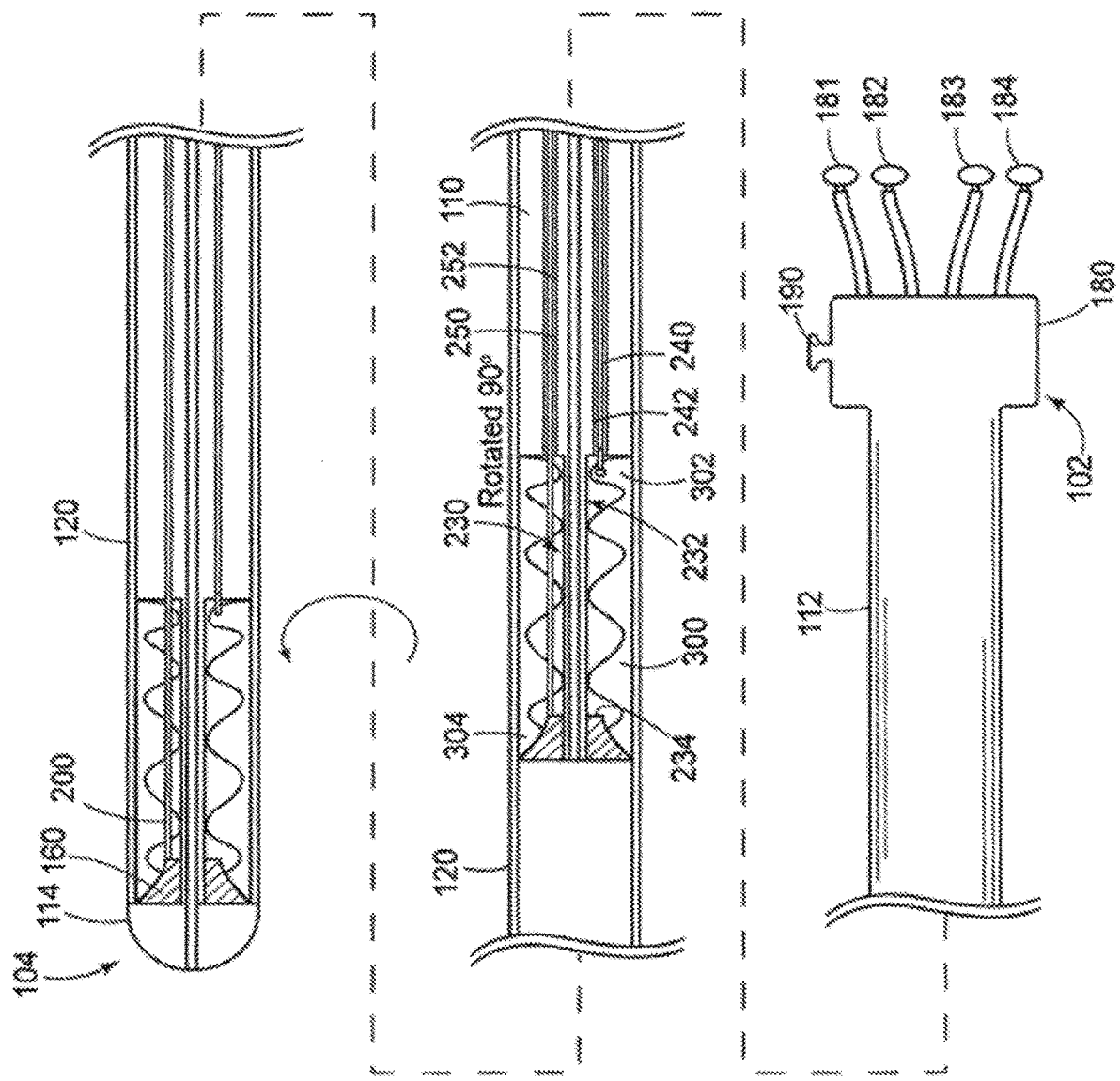

In accordance another embodiment, as depicted in FIG. 5, if desired, it is possible to provide a second deployable valve prosthesis 300. The technique for retaining, releasing and delivering the second prosthesis 300 may be very similar to the first prosthesis 200. The same sheath 120 may be used to house the second prosthesis 300 in cooperation with the elongate body 110 to define a second compartment 260 to store the second prosthesis 300 until it is deployed. In accordance with one example of this embodiment, the catheter 100 may further include a third linkage 240 extending from a proximal region of the second compartment 230 toward the proximal end 102 of the catheter 100 and a fourth linkage 250 extending from a distal region of the second compartment 230 toward the proximal end of the catheter 100. As depicted, the second prosthesis 300 has a proximal end 302 attached to the third linkage 240 and a distal end 304 attached to the fourth linkage 250.

Concerning the relative positioning of multiple prostheses 200, 300 on catheter 100, prostheses 200, 300 may be disposed in opposite orientations from one another rotationally. As depicted, for sake of convenience, prostheses 200, 300 are disposed on catheter 100 at a relative rotation of 90 degrees to permit linkages 140, 150, 240, 250 to each occupy a lumin (142, 152, 242, 252) in a different quadrant of the cross section of elongate body 110 as depicted in FIG. 3.

Elongate body 110 may be made in a variety of ways and from a variety of materials. For example, elongate body 110 may be made from a variety of materials, including metal, plastic and composite materials. Metal tubes such as stainless steel hypotubes can be used for one or more portions of elongate body 110 for enhanced pushability alone or in combination with other suitable materials. For example, FIG. 6 discloses a cross section of the elongate body 110 of the exemplary catheter illustrated in FIGS. 4-5, including a plurality of lumins that may be used for directing linkages to the distal region of the catheter. If metal tubular components are used to make elongate body 110, they are preferably coated with a lubricious material such as PTFE, other hydrophobic materials or hydrophilic materials. Multilayered polymeric tubes can also be used to form elongate member 110 that can be formed by co-extrusion, dipping processes, or by shrinking tubing layers over one another over a mandrel. Moreover, polymeric tubular members can also be formed by charging a mandrel with static electricity, applying plastic in powder or granular form to the mandrel to form a layer of plastic over the mandrel, and by heating the mandrel to cause the particles to fuse. Multilayered polymeric tubes can also be used that include metallic or nonmetallic braiding within or between layers of the tube. A carbon tube can also be used, as well as fiber-reinforced resin materials. In accordance with another embodiment, elongate body 110 may be provided with a decreasing stiffness along its length from proximal end 112 to distal end 114. As will be further appreciated by those of skill in the art, elongate body 110 may include a multiple-lumen extrusion including two, three, four, or more lumins along part of or substantially the entire length of elongate body 110 as depicted in FIG. 4. Moreover, stiffening wires can be used at various locations along elongate body to provide stiffness transitions between relatively stiffer regions and less stiff regions, as well as proximate regions of stress concentration, such as guidewire exit ports and the like. In accordance with one embodiment, a guidewire lumin 118 is provided along substantially the entire length of elongate body 110 as with typical over the wire ("OTW") catheters. In accordance with another embodiment, a guidewire lumin 118 is provided only proximate the distal region of elongate body 110 to permit use of catheter 100 as a rapid exchange ("RX") catheter.

Sheath 120 may be made from a variety of materials. Preferably, sheath 120 includes a multi-layered co-extrusion, such as those described in U.S. Pat. No. 6,464,683 to Samuelson or U.S. Pat. No. 5,538,510 to Fontirroche. Each of the aforementioned patents is incorporated by reference herein in its entirety.

As further depicted in FIG. 4, an actuator 170 is provided for selectively retracting sheath 120. Actuator 170 can take on a variety of forms, such as those depicted in U.S. Pat. No. 6,488,694 to Lau and U.S. Pat. No. 5,906,619 to Olson, the specifications of which are incorporated herein by reference. In addition, as depicted in FIGS. 4-5, a manifold 180 is provided including a plurality of actuators 181-184 for controlling linkages 140, 150, 240, 250. However, as will be appreciated, manifold may also include flush ports 190 for preparing or cleaning catheter 100.

Any surface of various components of the catheters described herein or portions thereof can be provided with one or more suitable lubricious coatings to facilitate procedures by reduction of frictional forces. Such coatings can include, for example, hydrophobic materials such as Polytetrafluoroethylene ("PTFE") or silicone oil, or hydrophilic coatings such as Polyvinyl Pyrrolidone ("PVP"). Other coatings are also possible, including, echogenic materials, radiopaque materials and hydrogels, for example.

Figure 7A:
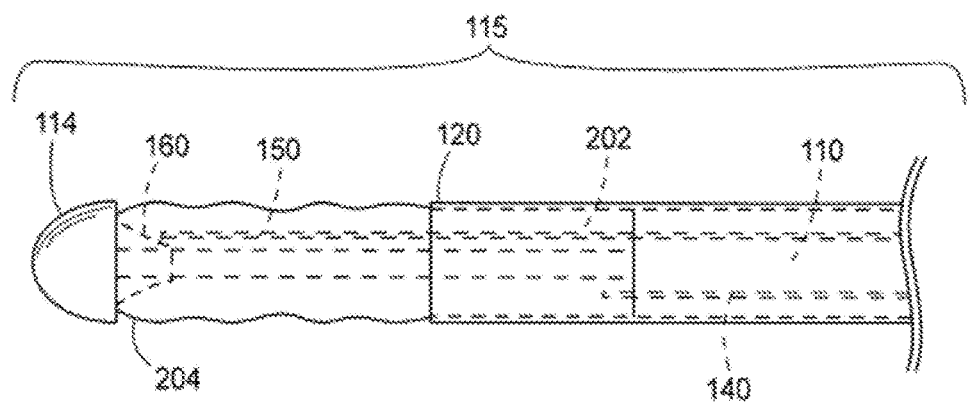
Figure 7B:
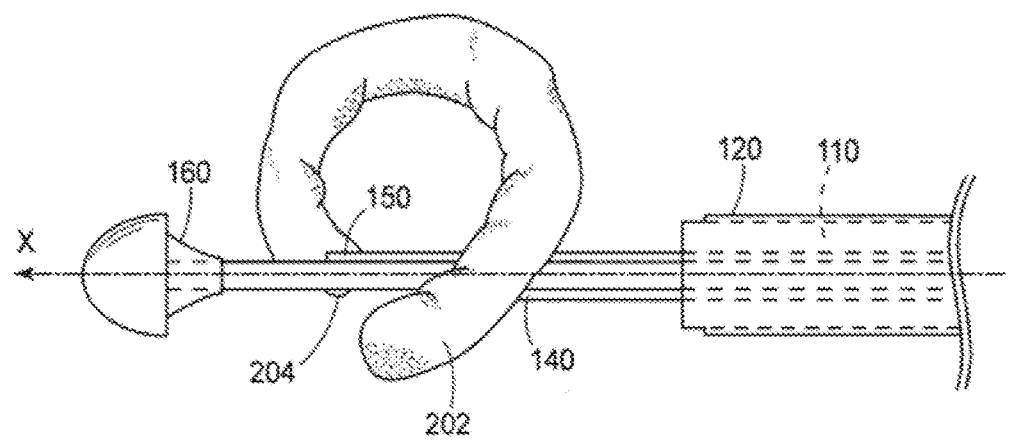

With reference to FIG. 7(A), a method for delivering a valve prosthesis includes advancing a distal portion 115 of a catheter 100 to a target location proximate a valve within a patient's luminal system. The method further includes withdrawing a sheath 120 on the catheter 100 to expose a valve prosthesis 200, the valve prosthesis 200 being in a generally longitudinal orientation prior to withdrawing the sheath 120. In some embodiments, the orientation is cross-sectional (not shown). Next, as illustrated in FIG. 7(B), the valve prosthesis is deformed from a pre-deployment, generally longitudinal orientation, into a second, generally arcuate orientation. In the embodiment of FIG. 7(B), this is accomplished by advancing linkage 140 distally, and advancing linkage 150 proximally. As can be seen this results in the first end 202 of the valve prosthesis 200 being drawn toward second end 204 of the valve prosthesis 200.

As depicted in FIG. 7(B), the valve prosthesis 200 may lie in a plane that is generally parallel to the longitudinal axis X of the catheter when the first end 202 of the valve prosthesis 200 is drawn toward the second end 204 of the valve prosthesis 200.

Figure 8:
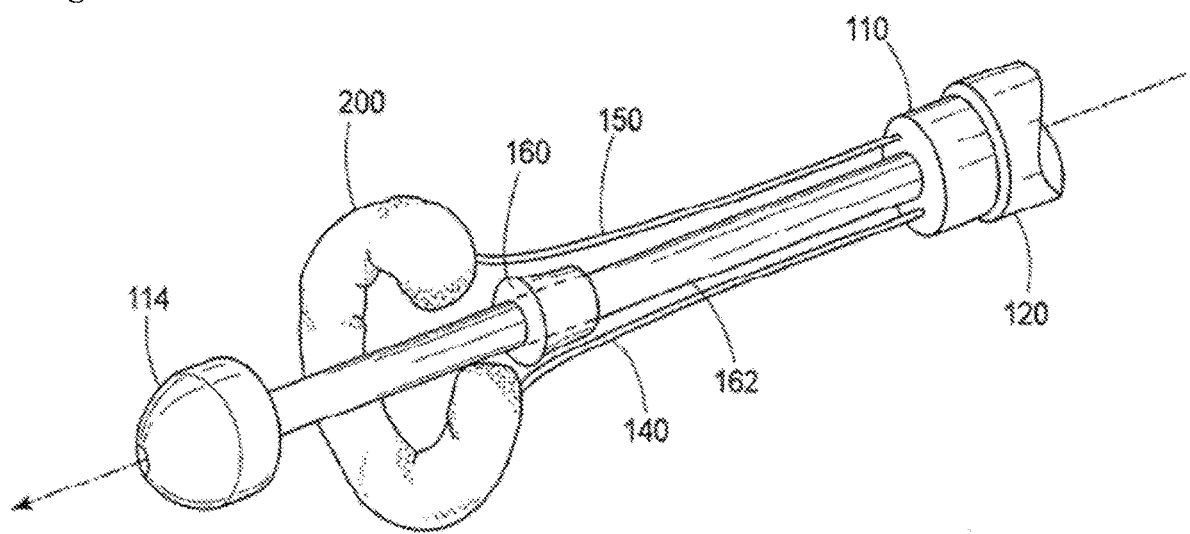

As illustrated in FIG. 8, the method can further include the step of rotating the valve prosthesis 200 out of the plane generally parallel to the longitudinal axis of the catheter into a plane that is generally perpendicular to the longitudinal axis of the catheter. As illustrated in FIG. 5, at this point, linkages 140, 150 are about the same distance from the proximal end of the catheter, but guide member 160 has not yet been fully actuated to continue deployment.

Figure 9:
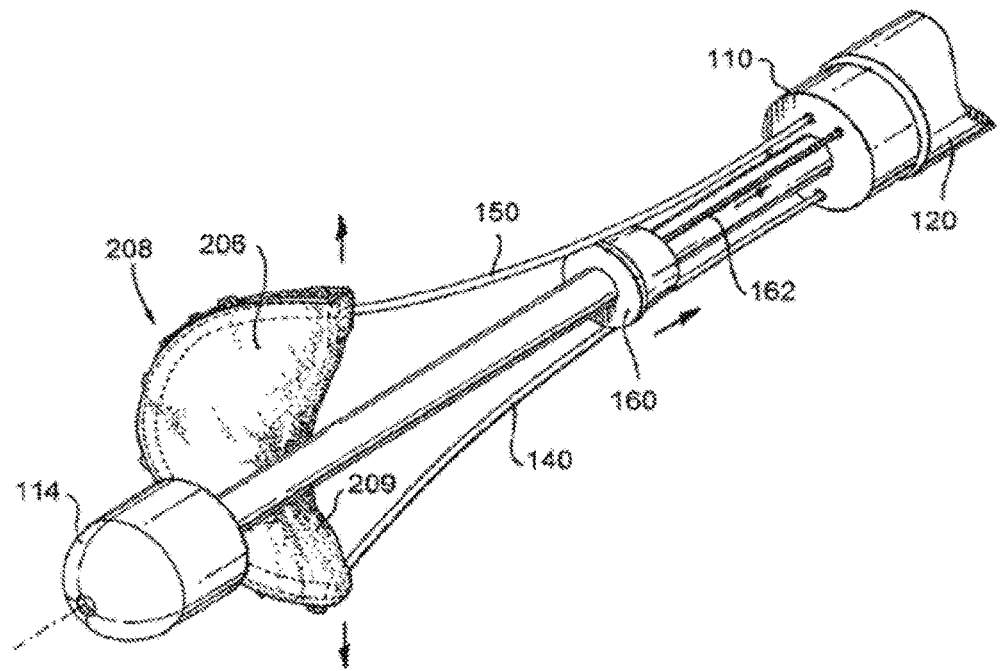
Figure 10:
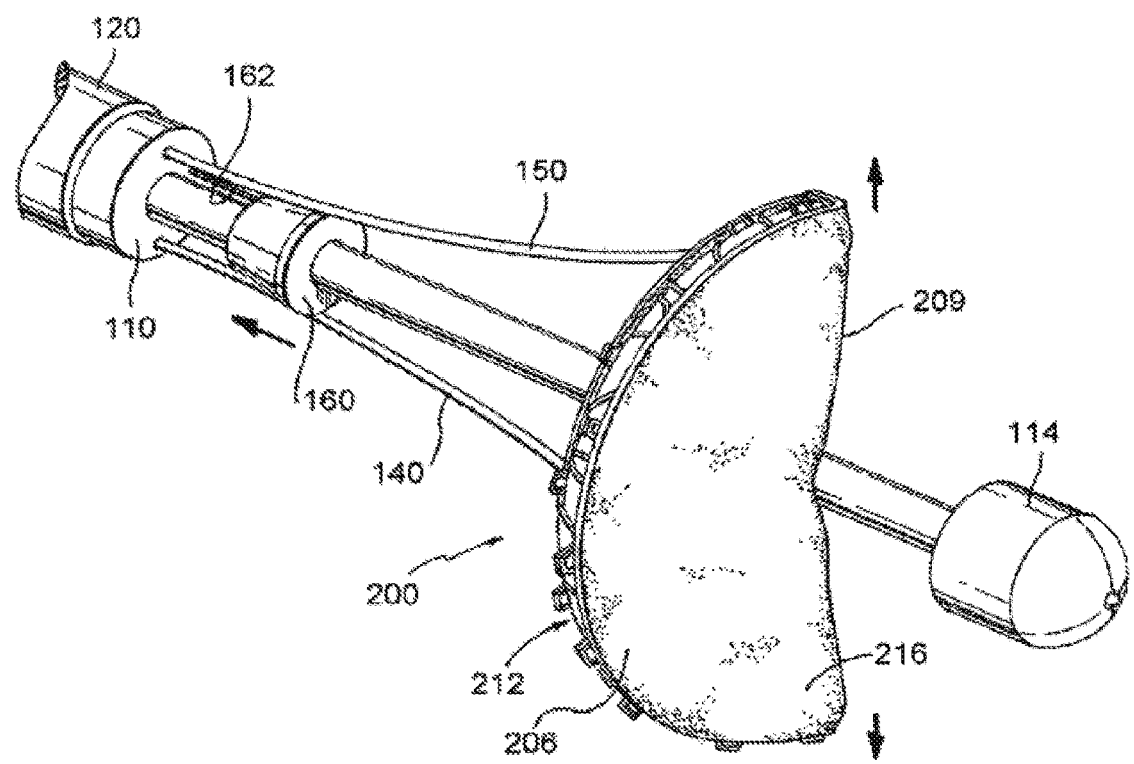

As depicted in FIG. 9, the method may further include deploying a guide member (e.g., 160 by pulling pull wire 162), to cause linkages 140, 150 to splay outwardly to cause prosthesis 200 to fully deploy into a condition illustrated in FIG. 10. At this point, prosthesis 200 can be positioned within a patient's valve annulus and secured by various retainers, such as sutures and clips. In accordance with one embodiment, prosthesis may simply be installed over the patient's existing valve leaflet, causing the pre-existing leaflet to be pinned to the side of the vessel wall. Once properly installed, edge 209 of leaflet 208 will substantially align with the adjoining pre-existing leaflet. However, if desired, a second prosthesis 300 may be installed proximate the first prosthesis to accomplish a full replacement. The second prosthesis 300 may be provided by using a catheter made in accordance with the teachings relating to FIG. 5 herein, or simply by using a second catheter made in accordance with the teachings relating to FIG. 4.

As will be appreciated by those of skill in the art, a variety of procedures may be accomplished using the teachings herein. For example, a catheter made in accordance with the teachings relating to FIG. 5 herein to perform partial valve replacements at adjacent valves in a patient's vein, such as for treating leg edema. Accordingly, the valve prostheses can be provided in different sizes to allow for the reduction in size in sequential venous valves to permit one catheter to be used to make two valve replacements.

Figure 11:
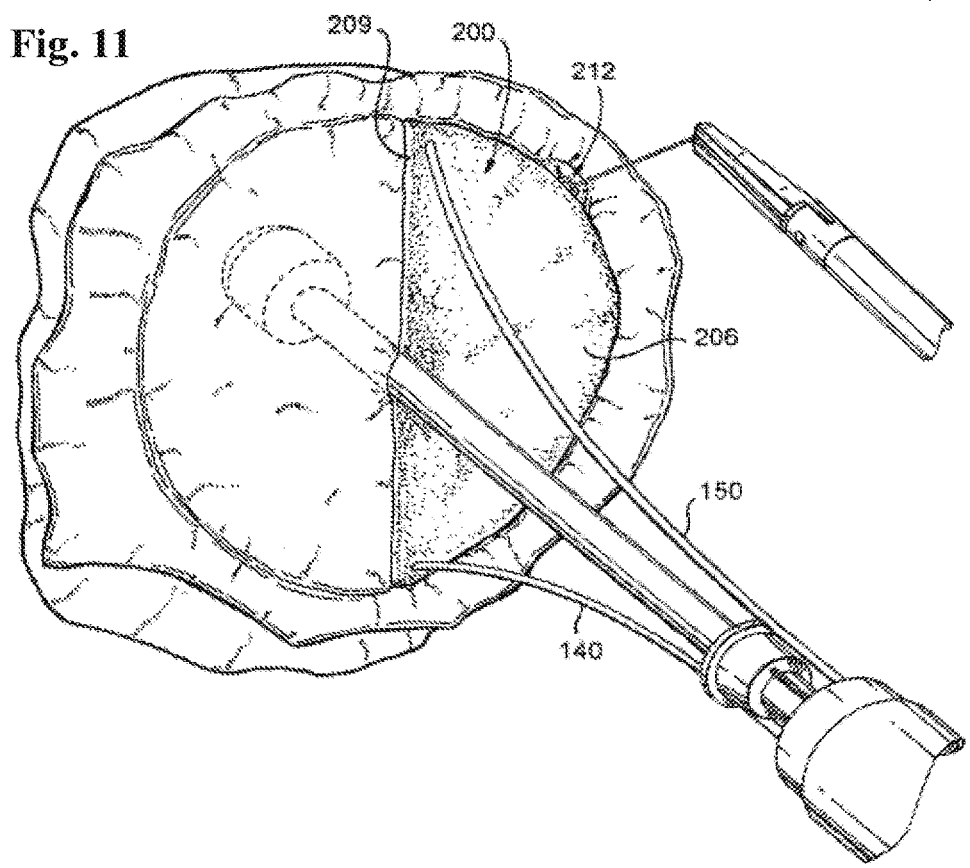
Figure 12:
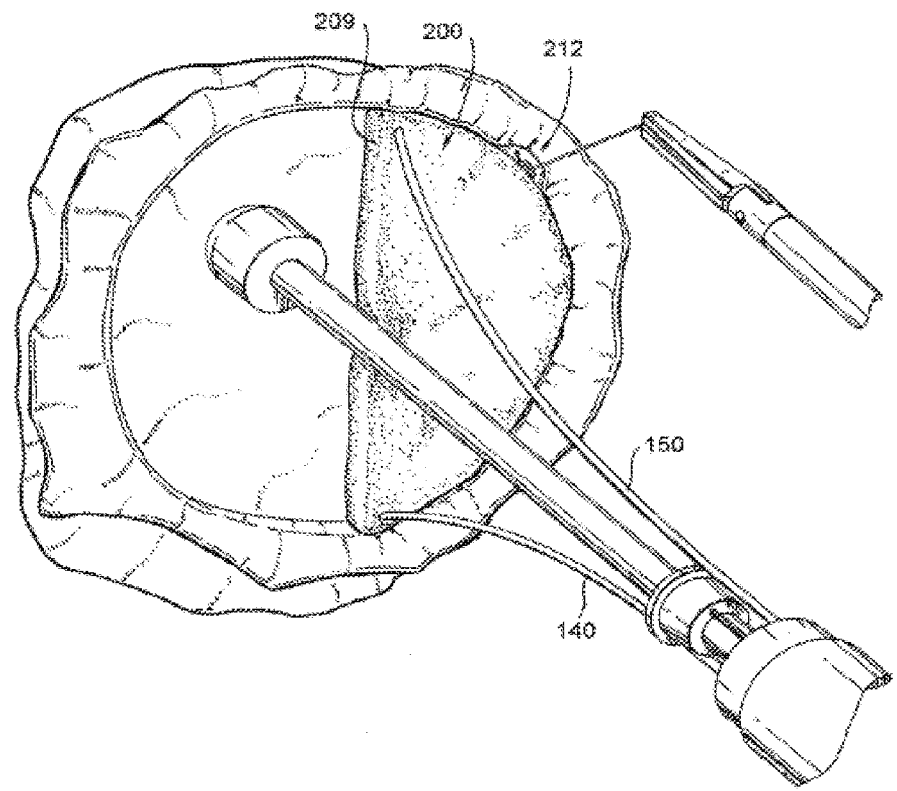
Figure 13:
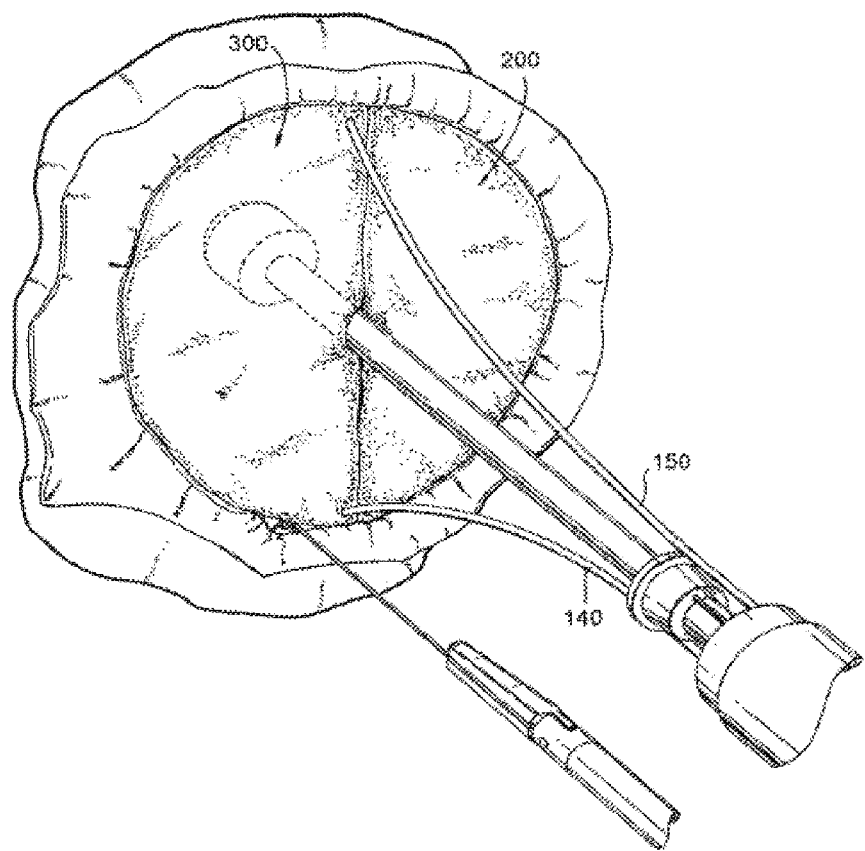

FIGS. 11-13 illustrate partial and complete valve replacement using embodiments of prosthesis made and installed in accordance with the present disclosure. FIG. 11 depicts a view of an exemplary prosthesis installed in a cardiac valve, such as a mitral valve, of an animal heart. The procedure depicted in FIG. 11 is one where a single prosthesis 200 is installed, replacing at least one of the valve leaflets. FIGS. 12-13 depicts a ventricular view of a similar procedure, but wherein both leaflets are replaced. In particular, FIG. 12 illustrates a single prosthesis installed, replacing one half of the valve, with the leaflet corresponding to the other half of the original valve being removed. FIG. 13 illustrates the addition of second valve prosthesis 300, resulting in a complete valve replacement, such as a mitral valve replacement. If desired, artificial valve chordae 273, 373 (such as sutures made of ePTFE or other suitable material) can be provided to connect the exposed edges 209, 309 of the leaflets to original chordae, or the papillary muscle where the original valve chordae were anchored.

Although the prior art prosthetic valves 10 (depicted in FIG. 3) exhibit differing approaches for securement, each of the embodiments are without regard for variations in the anatomy of a given valve. More specifically, each of the prior art prosthetic valves 10 are symmetric and therefore insensitive to variations between, for example, anatomical and physiological aspects of opposing leaflets in a bicuspid valve. In contrast, the teachings herein enable practitioners to account for differences in leaflet size, orientation, health and other such aspects. In some instances, a practitioner may wish to implant an embodiment of the prosthetic having only one leaflet, where that leaflet is designed to work with an existing natural leaflet. As one might imagine, such techniques can be substantially less invasive than insertion of one of the prior art prosthetic valves 10 depicted in FIG. 3, offering substantially better long term outcomes.

Figure 15A:
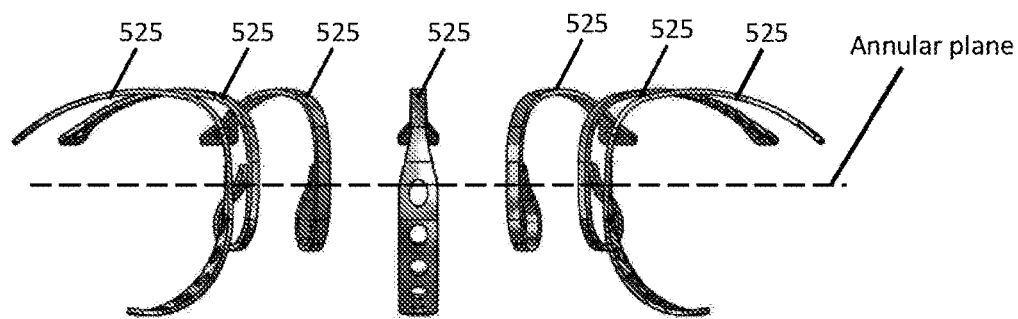
FIGS. 15A, 15B, 15C and 15D, collectively referred to herein as FIG. 15, depict aspects of an embodiment of yet another partial valve prosthesis as disclosed herein; and, FIG. 16 is a cross-sectional view of the mitral annulus depicting a portion of the partial valve prosthesis as disclosed in FIG. 15.
Figure 15B:
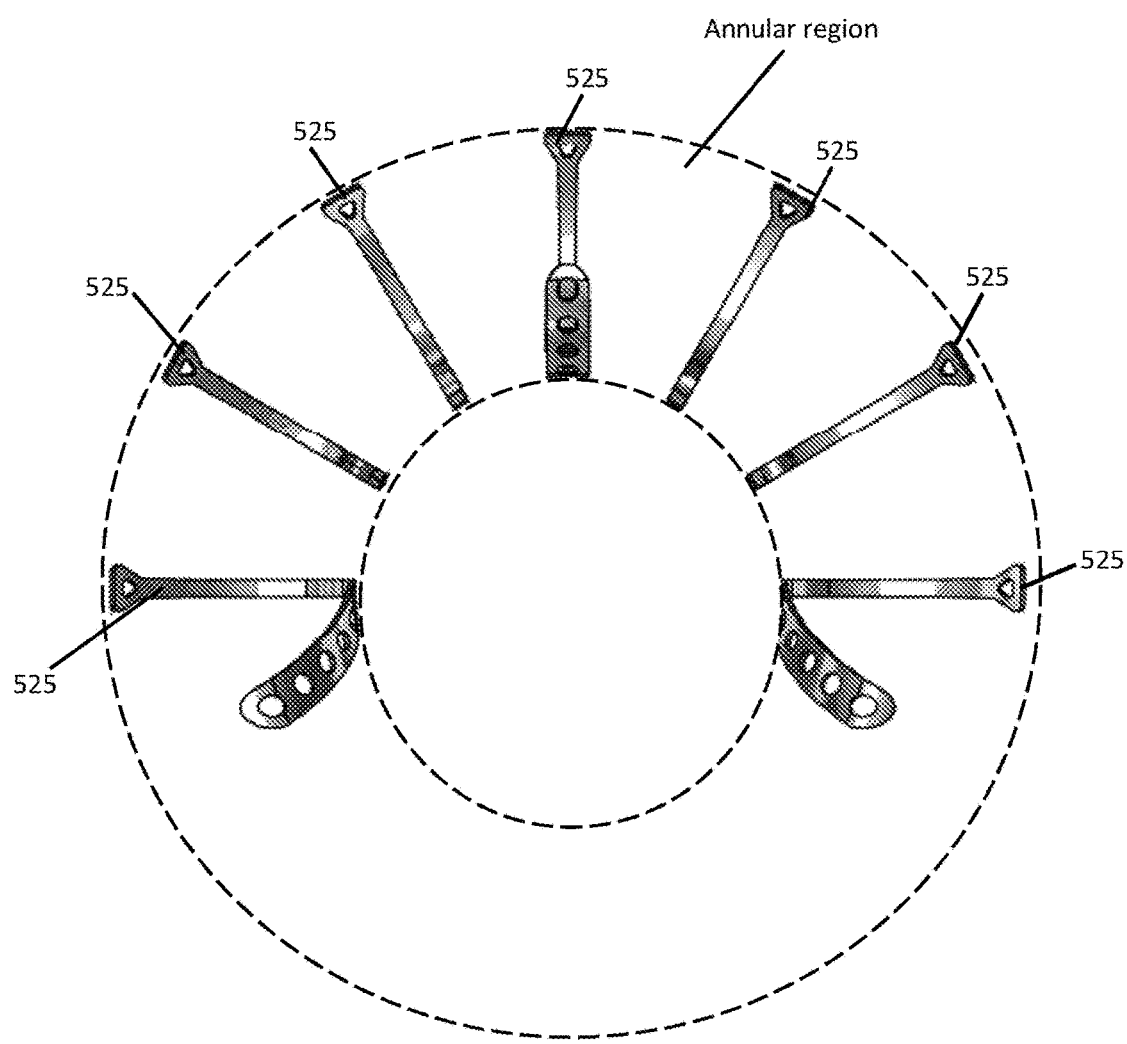
Figure 15C:
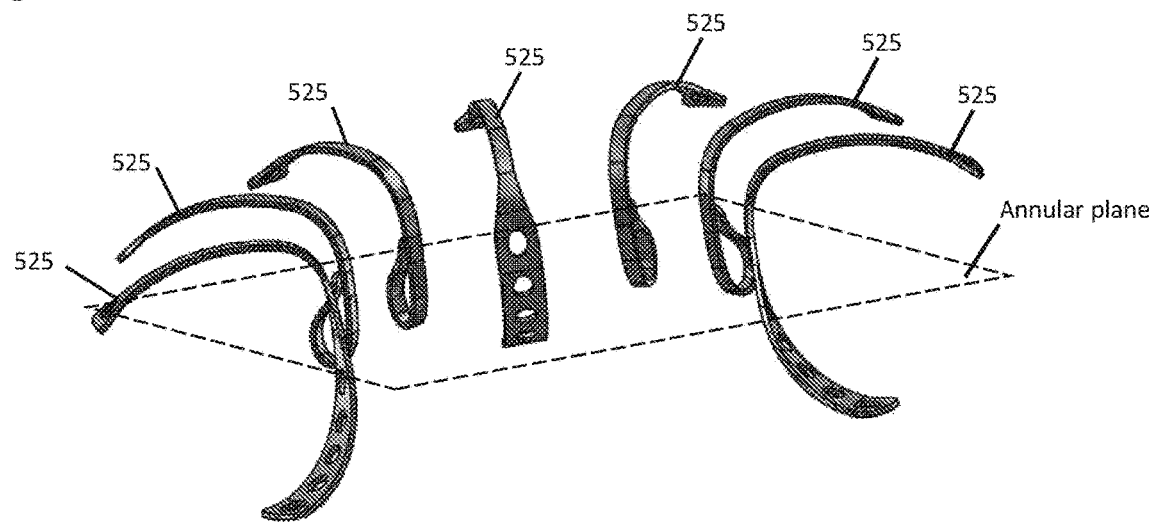
Figure 15D:
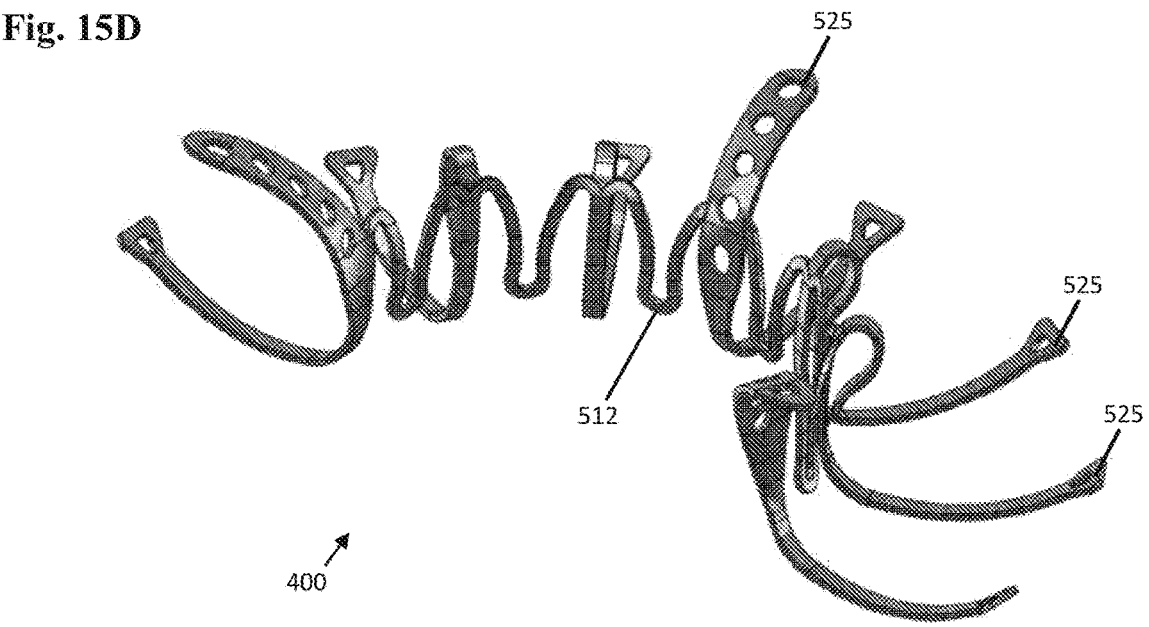
Figure 16:
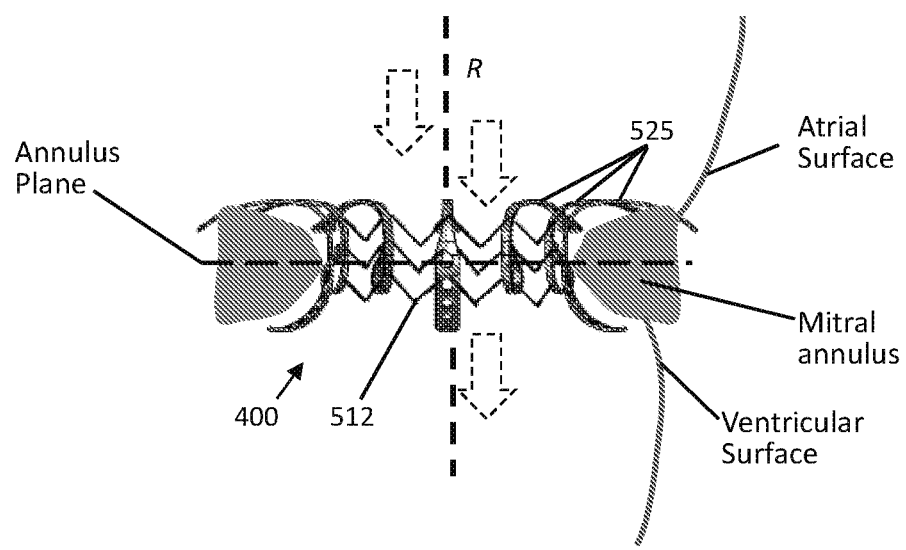

Embodiments of the C-shape or partial valve prosthesis disclosed herein may take advantage of a variety of anchoring or securement systems, such as those introduced in FIGS. 14-16. More specifically, the C-shape or partial valve prosthesis disclosed herein may include: a series of tines, petals, clamps, corkscrew anchors, cooperative stents, a cupped inlet side and combinations as deemed appropriate. In some embodiments, a series of clamps or clips may be used to anchor the C-shape prosthesis to the annulus of the valve selected for restoration. These additional anchors or securement features may be incorporated directly into the prosthesis and/or through use of intermediate structures or devices such as a cooperative stent, individual clamps, posts, fixation elements or the like. These and other techniques may be useful for anchoring or securing the C-shape prosthesis into the native mitral or tricuspid leaflet and/or annulus. Installation of intermediate structures may be in a two-part process using techniques such as multi-step delivery of components with various catheter devices.

Generally, the framework 412 serves as a structural element for retention of at least one leaflet. Generally, the framework 412 further includes anchoring features for securement of the partial valve prosthesis 400 when implanted. The anchoring features may include, for example, petal and other features presented elsewhere herein, and further may be designed for cooperation with secondary components, such as the posts (described below).

Figure 14A:
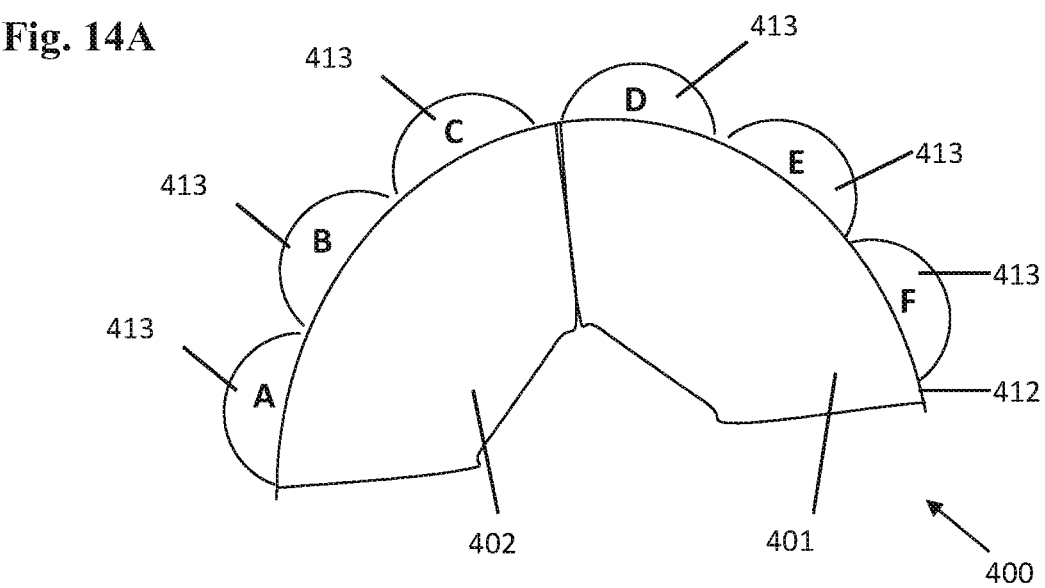
FIGS. 14A, 14B, and 14C, collectively referred to herein as FIG. 14, depict aspects of an embodiment of another partial valve prosthesis as disclosed herein.

Refer to FIG. 14 where a schematic, top-down view of an embodiment of the partial valve prosthesis 400 is shown. In the illustration of FIG. 14A, the partial valve prosthesis 400 includes a framework 412. Generally, the framework 412 is configured to fit substantially against an inner periphery of the annulus. The framework 412 may be fabricated from materials such as materials providing for shape memory effect (as described elsewhere herein). In this example, the framework 412 includes a series of petals 413. The petals 413 may also be fabricated from materials such as materials providing for shape memory effect. An overlay of sheathing material (as described elsewhere herein) may also be included. In this example of the partial valve prosthesis 400, a first leaflet 401 and a second leaflet 402 are included and a part of the partial valve prosthesis 400.

Figure 14B:
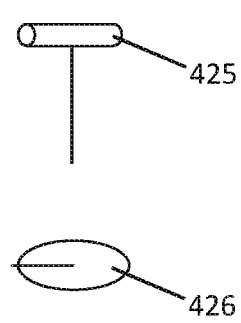

As shown in FIG. 14B, a series of posts 425 and fixation elements 426 may be used to secure the partial valve prosthesis 400 once the partial valve prosthesis 400 has been positioned in the patient. Generally, and as an example, a given one of the posts 425 may be disposed through a respective leaflet 413, piercing tissue of the annulus. The post 425 may be transitioned through the annular tissue and secured on an opposing side with a fixation element. An example of a similar type of fastener includes those used with earrings for pierced ears or unpierced ears. Of course, the scale, sharpness, material used and other properties may be varied as deemed appropriate. These posts may also be used for the securement of at least one leaflet, chordae or subvalvular structure to mimic native valve anatomy.

Figure 14C:
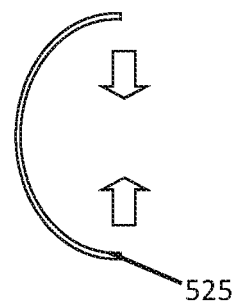

As shown in FIG. 14C, in some embodiments, a clamp 525 may be used. The clamp 525 may include an inward springing force (as depicted by the arrows) to provide for engagement of the annulus. The clamp 525 may be used alone or in conjunction with the post 425 and/or fixation element 426. Aspects of an embodiment of the partial valve prosthesis 400 involving use of a series of clamps 525 are depicted in FIG. 15.

In FIG. 15A and FIG. 15B, an array of clamps 525 are shown. In FIG. 15A, the array of clamps 525 is shown relative to the annular plane (an imaginary plane which bisects the annulus). The array of clamps 525 include a distribution of each of the clamps 525. Omitted from the illustrations of FIG. 15A and FIG. 15B is the framework which may be included to provide for enhanced integrity of the partial valve prosthesis 400. As may be seen from the illustrations, each of the clamp 525 may include at least one perforation. The perforations may be useful for setting of the post 425, use of suture or use of other techniques for securing the clamp 525. At least some of the clamps 525 may include terminate with a loop to facilitate fixation of a naive or native leaflet.

In some embodiments, each clamp 525 in the array of clamps 525 is delivered individually to a locus and set by the practitioner. Accordingly, the partial valve prosthesis 400 may be arranged using the array of clamps 525 to closely follow the contours of the annulus. This results in a seal between the partial valve prosthesis 400 and the annulus that has an efficacy not achieved in the prior art.

FIG. 15B is a top down view of the array of clamps 525 distributed about the annular region (i.e., the area containing the annulus). FIG. 15C provides a further view from an angular orientation. FIG. 15C provides another view with one embodiment of a framework 512. A variety of other embodiments for the framework 512 may be used in place of or in conjunction with the framework 512 illustrated.

In FIG. 16, further aspects of the partial valve prosthesis 400 of FIG. 15 are shown. In this illustration, portions of the partial valve prosthesis 400 are shown implanted into the mitral annulus. Included in this illustration is the framework 512. Each of the clamps 525 may be provided bound to the framework, thus the partial valve prosthesis 400 is a substantially unitary structure when implanted. In another embodiment, the partial valve prosthesis 400 may be assembled in-situ by a practitioner. For example, each of the clamps 525 may be clamped over the framework 512 in a sequential fashion during implantation.

Although disclosed with regard to a mitral annulus and mitral valve replacement or augmentation, the C-shape or partial prosthesis disclosed herein may be used in other situations as deemed appropriate. That is, as will be appreciated by those of skill in the art, the delivery catheters and associated methods described herein may be used to deliver a variety of devices within the luminal system of a patient. This approach permits implantation of relatively large devices, such as replacement valves for large lumins, on comparatively smaller profile catheters than used heretofore in the art. As such, it will be appreciated that such catheters and methods can be used to deliver such implants adapted (e.g., sized) for other applications, such as veins, arteries, the gastrointestinal tract, or any other body conduit/lumin that would benefit from such a valve apparatus.

Having introduced embodiments of a C-shape or partial valve prosthesis, some additional aspects are now disclosed.

In some embodiments, the partial valve prosthesis is attached to a native leaflet and/or annulus, or a portion thereof. For example, the partial valve prosthesis may be configured to clamp onto a remaining portion of a native leaflet.

The at least one leaflet for the partial valve prosthesis may be attached to the framework by any one or more of a variety of techniques. For example, the at least one leaflet may be sewn to the framework and/or clamps. The at least one leaflet may be attached to the framework and/or clamps by use of the posts, clips or by other techniques as deemed appropriate.

The teachings herein are particularly effective for replacement of the posterior leaflet of the mitral valve, and the anterior and posterior leaflet of the tricuspid valve.

In some embodiments, the chordae tendineae are attached to the at least one leaflet of the partial valve prosthesis, thus further minimizing prolapse and other chronic and debilitating conditions. By configuring the partial valve prosthesis to follow the inner periphery of the native valve annulus and/or cooperate with the chordae tendineae, the partial valve prosthesis is regarded as mimicking the physiology of the natural valve.

It should be recognized that the native valve leaflets extend from the native valve annulus. Accordingly, it may not be possible, in at least some instances, to clearly distinguish between the native valve leaflets and the native valve annulus. Thus, it should be recognized that in at least some instances, the terminology may be synonymous or substantially related. For example, in some instances, the partial valve prosthesis may be secured to what may be regarded as a base of the native valve leaflet (i.e., the leaflet itself), which is proximate to the native valve annulus. Thus, as discussed herein, securement of the native valve prosthesis is not to be limited by language calling for securement to the annulus and may include securement to at least a portion of the native valve leaflet. Conversely, in some instances, a practitioner can clearly distinguish the point of securement.

In some embodiments, the C-shape or partial valve prosthesis is delivered via the catheter as an elongate structure. In some other embodiments, the partial valve prosthesis is delivered by a different type of catheter tool. For example, in a first stage, the catheter may deliver a stent or framework for the partial valve prosthesis. In a second stage, the catheter may deliver a series of fasteners for fastening the partial valve prosthesis to the annulus.

In some other embodiments, the C-shape or partial valve prosthesis is delivered in a final state. That is, the C-shape or partial valve prosthesis is delivered is not provided in a first form and then in a deployed form. Rather, the C-shape or partial valve prosthesis is delivered in a final configuration. The C-shape or partial valve prosthesis may be delivered in a partially collapsed configuration. For example, the C-shape or partial valve prosthesis may have an expandable framework that is set once properly positioned. The C-shape or partial valve prosthesis may be assembled in place with multiple deliveries of components.

The posts may have a straight shaft, a curved shape or exhibit any shape deemed appropriate. The posts may include features, such as barbs, to provide for or enhance securement.

In some embodiments, the series of fasteners may be delivered as a package, effectively contained within a pouch of sheathing material. Once the series of fasteners is distributed and implanted, the pouch serves as the protective sheathing for the assembled partial valve prosthesis.

Various other components may be included and called upon for providing for aspects of the teachings herein. For example, additional materials, combinations of materials and/or omission of materials may be used to provide for added embodiments that are within the scope of the teachings herein.

A variety of modifications of the teachings herein may be realized. Generally, modifications may be designed according to the needs of a user, designer, manufacturer or other similarly interested party. The modifications may be intended to meet a particular standard of performance considered important by that party.

When introducing elements of the present invention or the embodiment(s) thereof, the articles "a," "an," and "the" are intended to mean that there are one or more of the elements. Similarly, the adjective "another," when used to introduce an element, is intended to mean one or more elements. The terms "including" and "having" are intended to be inclusive such that there may be additional elements other than the listed elements. As used herein, the term "exemplary" is not intended to imply a superlative example. Rather, "exemplary" refers to an embodiment that is one of many possible embodiments.

While the invention has been described with reference to exemplary embodiments, it will be understood by those skilled in the art that various changes may be made and equivalents may be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

It should be understood at the outset that, although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described below.

Unless otherwise specifically noted, articles depicted in the drawings are not necessarily drawn to scale.

Modifications, additions, or omissions may be made to the systems, apparatuses, and methods described herein without departing from the scope of the disclosure. For example, the components of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set.

To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

What is claimed is:

1. A partial valve prosthesis to replace a portion of a native luminal valve, the native luminal valve defining a native valve annulus and a plurality of native leaflets, the partial valve prosthesis comprising:
   a framework configured to follow a shape of a portion of the native valve annulus when implanted into the native valve annulus, the framework including an array of scaffolding members attached thereto, each of the scaffolding members including an elongate metallic body and having a first end extending superiorly so as to secure the framework above the native valve annulus and a second end extending inferiorly so as to secure the framework below the native valve annulus, the scaffolding members being configured for arrangement about a portion of the native valve annulus for anchoring the prosthesis to an inner periphery of the native valve annulus, the framework being further configured to retain at least one valve leaflet configured to replace a corresponding one of the plurality of native leaflets; and at least one leaflet secured to the framework, wherein the at least one leaflet is configurable between a closed configuration and an open configuration, wherein the at least one leaflet is movable in a first direction into coaptation with an opposed native leaflet in the closed configuration, and wherein the at least one leaflet is movable in a second opposite direction away from the opposed native leaflet in the open configuration;

wherein the scaffolding members include a central scaffolding member and a terminal scaffolding member positioned on both sides of the central scaffolding member and wherein the central scaffolding member and both terminal scaffolding members each include an extended second end extending inferiorly beyond the second ends of remaining scaffolding members.

2. The partial valve prosthesis as in claim 1, wherein at least one of the scaffolding members includes at least one of a perforation and a loop at the respective first end or second end of said at least one of the scaffolding members.

3. The partial valve prosthesis as in claim 1, wherein at least one of the scaffolding members defines a perforation therethrough at the first or second end of the scaffolding member, and further wherein a fastener is directed through said perforation.

4. The partial valve prosthesis as in claim 1, wherein the native luminal valve is a mitral valve.

5. The partial valve prosthesis as in claim 1, wherein the native luminal valve is a tricuspid valve.

6. The partial valve prosthesis as in claim 1, wherein the native luminal valve is an aortic valve.

7. The partial valve prosthesis as in claim 1, wherein the prosthesis is configured to mimic the physiology of the native luminal valve.

8. The partial valve prosthesis as in claim 1, further comprising a protective sheathing disposed over at least a portion of the partial valve prosthesis.

9. The partial valve prosthesis as in claim 8, wherein the protective sheathing includes at least one of polytetrafluoroethylene (PTFE) and polyethylene terephthalate.

10. The partial valve prosthesis as in claim 1, wherein the first end is configured to apply a first pressure to a superior surface of the native valve annulus and the second end is configured to apply a second pressure to an inferior surface of the native valve annulus.

11. The partial valve prosthesis as in claim 1, further comprising at least one tissue anchor configured to connect to the scaffolding members.

12. The partial valve prosthesis as in claim 11, wherein the framework is securable to the native valve annulus via the at least one tissue anchor and the scaffolding members.

13. The partial valve prosthesis as in claim 11, wherein the at least one tissue anchor comprises a post and a fixation element for securement to the post.

14. The partial valve prosthesis as in claim 1, wherein the first end and the second end are configured to generate a spring force for engaging with the native valve annulus.

15. A partial valve prosthesis for replacing a portion of a native luminal valve, the native luminal valve defining a native valve annulus and a plurality of native leaflets, the partial valve prosthesis comprising:

a framework configured to follow a shape of a portion of the native valve annulus when implanted into the native valve annulus, the framework including an array of scaffolding members attached thereto, each of said scaffolding members having an elongate flattened body biased to clamp closed by a springing force, each of said scaffolding members having a first end biased to clamp above the native valve annulus and a second end biased to clamp below the native valve annulus, each of the scaffolding members being arranged to clamp about at least a portion of one of the native valve annulus and at least one of the native leaflets, the framework further comprising at least one leaflet configured to replace the at least one native leaflet to which it is clamped such that the at least one leaflet is movable into coaptation with a native leaflet opposite to the at least one native leaflet clamped via the scaffolding members;

wherein the scaffolding members include a central scaffolding member and a terminal scaffolding member positioned on both sides of the central scaffolding member and wherein the central scaffolding member and both terminal scaffolding members each include an extended second end extending inferiorly beyond the second ends of remaining scaffolding members.

16. The partial valve prosthesis as in claim 15, wherein the native luminal valve is a mitral valve.

17. The partial valve prosthesis as in claim 15, wherein the native luminal valve is a tricuspid valve.

18. The partial valve prosthesis as in claim 15, wherein the native luminal valve is an aortic valve.

19. The partial valve prosthesis as in claim 15, wherein the prosthesis is configured to mimic the physiology of the native luminal valve.

20. The partial valve prosthesis as in claim 15, further comprising a protective sheathing disposed over at least a portion of the partial valve prosthesis.

21. The partial valve prosthesis as in claim 20, wherein the protective sheathing includes at least one of polytetrafluoroethylene (PTFE) and polyethylene terephthalate.

22. A partial valve prosthesis for replacing a portion of a native luminal valve, the native luminal valve defining a native valve annulus and a plurality of native leaflets, the partial valve prosthesis comprising:

a framework configured to follow a shape of a portion of the native valve annulus when implanted into the native valve annulus, the framework including one or more scaffolding members attached thereto, each of said scaffolding members having an elongate body biased to clamp against tissue by a springing force, each of said scaffolding members having a first end extending superiorly and biased to clamp above the native valve annulus and a second end extending inferiorly and biased to clamp below the native valve annulus, each of the scaffolding members being arranged to clamp about at least a portion of one of the native valve annulus and a portion of one of the native leaflets, the framework further comprising at least one leaflet configured to replace the at least one native leaflet to which it is clamped such that the at least one leaflet has a width which is no more than half of a periphery of the native valve annulus, wherein the scaffolding members are clamped over the framework; and at least one tissue anchor configured to connect to the scaffolding members such that the framework is securable to the native valve annulus via the at least one tissue anchor and the scaffolding members;

wherein the scaffolding members include a central scaffolding member and a terminal scaffolding member positioned on both sides of the central scaffolding member and wherein the central scaffolding member and both terminal scaffolding members each include an extended second end extending inferiorly beyond the second ends of remaining scaffolding members.

23. The partial valve prosthesis as in claim 22, wherein the native luminal valve is a mitral valve.

24. The partial valve prosthesis as in claim 22, wherein the native luminal valve is a tricuspid valve.

25. The partial valve prosthesis as in claim 22, wherein the native luminal valve is an aortic valve.

* * * * *